(12) United States Patent
Peine et al.

(10) Patent No.: US 12,082,898 B2
(45) Date of Patent: Sep. 10, 2024

(54) HAND EYE COORDINATION SYSTEM FOR ROBOTIC SURGICAL SYSTEM

(71) Applicant: Covidien LP, Mansfield, MA (US)

(72) Inventors: William J. Peine, Ashland, MA (US); Stefan Joerg, Wessling (DE); Paul M. Loschak, Somerville, MA (US)

(73) Assignee: Covidien LP, Mansfield, MA (US)

( * ) Notice: Subject to any disclaimer, the term of this patent is extended or adjusted under 35 U.S.C. 154(b) by 551 days.

(21) Appl. No.: 17/421,753

(22) PCT Filed: Feb. 4, 2020

(86) PCT No.: PCT/US2020/016487
§ 371 (c)(1),
(2) Date: Jul. 9, 2021

(87) PCT Pub. No.: WO2020/163263
PCT Pub. Date: Aug. 13, 2020

(65) Prior Publication Data
US 2022/0022984 A1    Jan. 27, 2022

Related U.S. Application Data

(60) Provisional application No. 62/801,734, filed on Feb. 6, 2019.

(51) Int. Cl.
*A61B 34/37* (2016.01)
*A61B 34/30* (2016.01)
*A61B 90/00* (2016.01)

(52) U.S. Cl.
CPC .............. *A61B 34/37* (2016.02); *A61B 34/30* (2016.02); *A61B 90/361* (2016.02); *A61B 90/37* (2016.02); *A61B 2090/368* (2016.02)

(58) Field of Classification Search
CPC ....... A61B 34/37; A61B 34/30; A61B 90/361; A61B 90/37; A61B 2090/368
See application file for complete search history.

(56) References Cited

U.S. PATENT DOCUMENTS 8,828,023 B2    9/2014  Neff et al.
2012/0265071 A1  10/2012  Berke
(Continued)

FOREIGN PATENT DOCUMENTS

KR    10-2016-0013533 A    2/2016
WO         03064116 A2    8/2003
(Continued)

OTHER PUBLICATIONS

Office Action dated Jun. 4, 2023 for Chinese Patent Application No. 202080008154.9 (18 pages).
(Continued)

*Primary Examiner* — Jason Holloway
*Assistant Examiner* — Christopher A Buksa
(74) *Attorney, Agent, or Firm* — Carter, DeLuca & Farrell LLP

(57) ABSTRACT

A method of controlling a tool of a surgical robot with a processing unit such that the tool follows input of the input handle of a user console includes receiving movement of the input handle in a master frame of the user console, translating the movement of the input handle in the master frame to movement of the tool in a camera frame of a camera providing real-time images of a surgical site, translating the movement of the tool in the camera frame to movement of the tool in a world frame defined in a surgical theater, translating the movement of the tool in the world frame to movement of the tool in a tool frame which is defined by an arm supporting the tool, and transmitting control commands (Continued)

to a motor controlling the tool such that the tool follows movement of the input handle.

19 Claims, 5 Drawing Sheets

(56) References Cited

U.S. PATENT DOCUMENTS

| | | | |
|---|---|---|---|
| 2012/0290134 A1 | 11/2012 | Zhao et al. | |
| 2013/0331644 A1 | 12/2013 | Pandya et al. | |
| 2014/0276950 A1 | 9/2014 | Smaby et al. | |
| 2014/0378995 A1 | 12/2014 | Kumar et al. | |
| 2017/0095295 A1* | 4/2017 | Overmyer | B25J 13/02 |

FOREIGN PATENT DOCUMENTS

| | | |
|---|---|---|
| WO | 2012151585 A2 | 11/2012 |
| WO | 2017210074 A1 | 12/2017 |
| WO | 2017210499 A1 | 12/2017 |
| WO | 2020214193 A1 | 10/2020 |

OTHER PUBLICATIONS

Extended European Search Report dated Dec. 9, 2022 corresponding to counterpart Patent Application EP 20752590.8.

Columbia University: "Coordinate Frames and Transforms: 1 Specifiying Position and Orientation", Dec. 26, 2017 (Dec. 26, 2017), XP093004235, Retrieved from the Internet: URL:http://web.archive.org/web/20171226/https://www.cs.columbia.edu/~allen/F17/NOTES /frames2.pdf [retrieved on Dec. 1, 2022] * the whole document *.

International Search Report mailed 27, 2020 and Written Opinion completed May 27, 2020 corresponding to counterpart Int'l Patent Application PCT/US2020/016487.

Tobii, e-book, tech.tobii.com. Copyright 2021, Tobii AB, "5 Ways Next-Generation Surgical Robotics Will Leverage Attention to Enhance Care", pp. 1/12-12/12.

Tobii, Tobii White Paper, tech.tobii.com., May 2020, Version 1.0, "Why Next-Generation Surgical Systems Will Include Eye Tracking", pp. 1/15-15/15.

* cited by examiner

HAND EYE COORDINATION SYSTEM FOR ROBOTIC SURGICAL SYSTEM

CROSS-REFERENCE TO RELATED APPLICATIONS

The present application is a U.S. National Stage Application filed under 35 U.S.C. § 371(a) claiming the benefit of and priority to International Patent Application No. PCT/US2020/016487, filed Feb. 4, 2020, which claims the benefit of and priority to U.S. Provisional Patent Application Ser. No. 62/801,734, filed Feb. 6, 2019, the entire disclosures of each of which being incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system and a display allowing the surgeon to visualize the end effector within a surgical site. The visualization of the surgical site is provided by one or more cameras, e.g., endoscopes, that provide real-time images of the surgical site.

There is a continuing need for improved visualization of the surgical site and intuitive control of the surgical robot.

SUMMARY

This disclosure relates generally to methods for transforming movement of an input handle of a user console to movement of a tool of a surgical robot such that the tool moves as intended and as viewed on a display of the user console.

In an aspect of the present disclosure, a method of controlling a tool of a surgical robot with a processing unit such that the tool follows input of the input handle of a user console includes receiving movement of the input handle in a master frame of the user console, translating the movement of the input handle in the master frame to movement of the tool in a camera frame of a camera that provides real-time images of a surgical site, translating the movement of the tool in the camera frame to movement of the tool in a world frame defined in a surgical theater, translating the movement of the tool in the world frame to movement of the tool in a tool frame which is defined by an arm that supports the tool, and transmitting control commands to a motor that controls the tool such that the tool follows movement of the input handle.

In aspects, translating the movement of the input handle in the master frame to movement of the tool in the camera frame includes applying a display rotation matrix to movement of the input handle in the master frame to translate movement of the input handle to a display frame of a display of the user console. The display may provide visualization of the real-time images of the surgical site. The display rotation matrix may rotate the movement 30 degrees about an axis of the master frame.

In some aspects, translating the movement of the input handle in the master frame to movement of the tool in the camera frame includes applying a flip rotation matrix to movement of the input handle in the master frame to translate movement of the input handle to the camera frame. The flip rotation matrix may rotate movement 180 degrees about an axis of the display frame. The method may include receiving a flip flag and applying flip rotation matrix when the flip flag indicates that the real-time images from the camera are flipped before being viewed on a display.

In certain aspects, translating the movement of the tool in the camera frame to movement of the tool in the world frame includes determining yaw and pitch angles of the camera frame relative to the world frame and applying a world frame rotation matrix that includes the yaw and pitch angles of the camera frame relative to the world frame to translate the movement of the tool in the camera frame to movement of the tool in the world frame.

In particular aspects, translating the movement of the tool in the camera frame to the movement of the tool in the world frame includes receiving an offset of the camera and adjusting the movement in the camera frame by the offset of the camera by applying an adjustment rotation matrix that includes the offset of the camera to the movement of the tool in the camera frame.

In some aspects, translating the movement of the tool in the world frame to movement of the tool in the tool frame includes determining yaw and pitch angels of the tool frame relative to the world frame and applying a transpose of a tool frame rotation matrix that includes the yaw and pitch angles of the tool frame relative to the world frame to translate the movement of the tool in the world frame to movement of the tool frame. The method may include verifying the camera is fixed during the movement of the input handle before transmitting the control commands to the motor controlling the tool.

In another aspect of the present disclosure, a robotic surgical system includes a surgical robot, a user console, and a processing unit. The surgical robot includes a first arm that supports a camera and a second arm that supports a tool. The camera defines a camera frame and is configured to capture real-time images of a surgical site. The second arm defines a tool frame and is configured to manipulate the tool within the tool frame and the surgical robot defines a world frame. The user console includes an input handle and a display. The input handle is moveable within a master frame that is defined by the user console. The display is configured to display real-time images of the surgical site provided by the camera. The processing unit is configured to receive movement of the input handle in the master frame, translate the movement of the input handle in the master frame to movement of the tool in the camera frame, translate the movement of the tool in the camera frame to movement of the tool in the world frame, translate the movement of the tool in the world frame to movement of the tool in the tool frame, and transmit control commands to the second arm such that the tool follows movement of the input handle.

In aspects, the display defines a display frame that is rotated relative to one axis of the master frame. The display may be rotated 30 degrees about the one axis of the master frame. The processing unit is configured to apply a display rotation matrix to movement of the input handle in the master frame to translate movement of the input handle to the display frame.

In some aspects, the display is configured to flip the real-time images provided by the camera 180 degrees before displaying the real-time images. The processing unit is configured to receive a flip flag indicative of the real-time images being flipped on the display and to apply a flip rotation matrix to movement of the tool to translate the movement of the tool to the camera frame.

In certain aspects, the processing unit is configured to receive yaw and pitch angles of the camera frame relative to the world frame and to apply a world frame rotation matrix including the yaw and pitch angles of the camera frame relative to the world fame to translate the movement of the tool in the camera frame to movement of the tool in the world frame. The processing unit may be configured to receive an offset angle of the camera and to apply an adjustment rotation matrix including the offset angle of the camera to adjust the movement of the tool in the camera frame.

In particular aspects, the processing unit is configured to receive yaw and pitch angles of the tool frame relative to the world frame and to apply a transpose of a tool frame rotation matrix including the yaw and pitch angles of the tool frame relative to the world frame to translate the movement of the tool in the world frame to movement of the tool in the tool frame. The processing unit may be configured to verify the camera is fixed during the movement of the input handle before transmitting the control commands.

In another aspect of the present disclosure, a computer-readable medium has stored sequences of instructions that, when executed by a processor, cause the processor to receive movement of an input handle in a master frame of a user console, translate the movement of the input handle in the master frame into movement of a tool in a camera frame of a camera that provides real-time images of a surgical site, translate the movement of the tool in the camera frame to movement of the tool in a world frame that is defined in a surgical theater, translate the movement of the tool in the world frame to movement of the tool in a tool frame which is defined by an arm that supports the tool, and transmit control commands to a motor that controls the tool such that the tool follows movement of the input handle.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
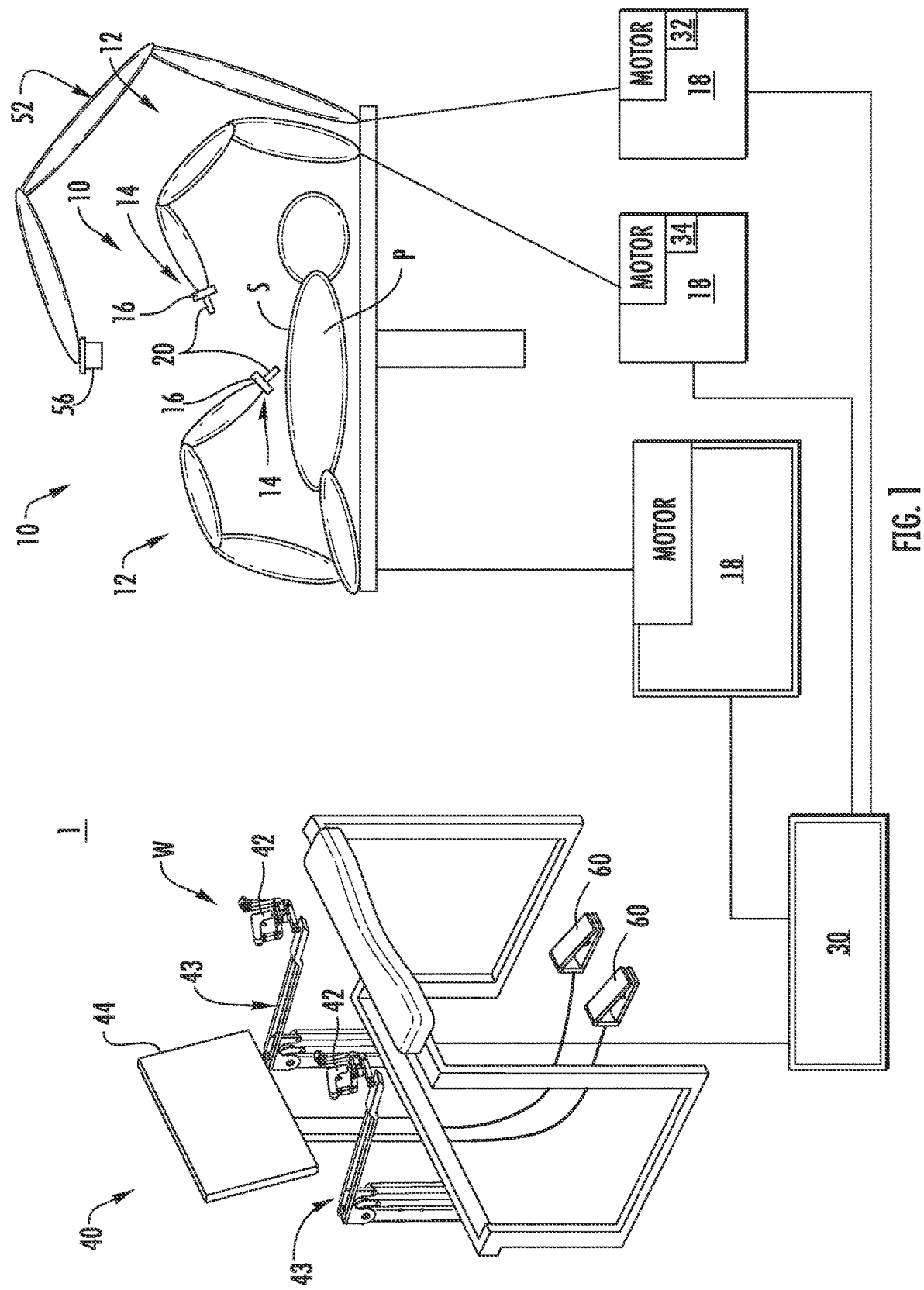
FIG. 1 is a schematic view of a robotic surgical system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel.

Referring to FIG. 1, a robotic surgical system 1 in accordance with the present disclosure is shown generally as a surgical robot 10, a processing unit 30, and a user console 40. The surgical robot 10 generally includes linkages or arms 12 and one or more robot bases 18. The linkages 12 moveably support an end effector or tool 20 which is configured to act on tissue. The linkages 12 may be in the form of arms each having an end 14 that supports the end effector or tool 20 which is configured to act on tissue. In addition, the ends 14 of the linkages 12 may include an imaging device 16 for imaging a surgical site "S". The user console 40 is in communication with the robot bases 18 through the processing unit 30.

The user console 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "5". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2:
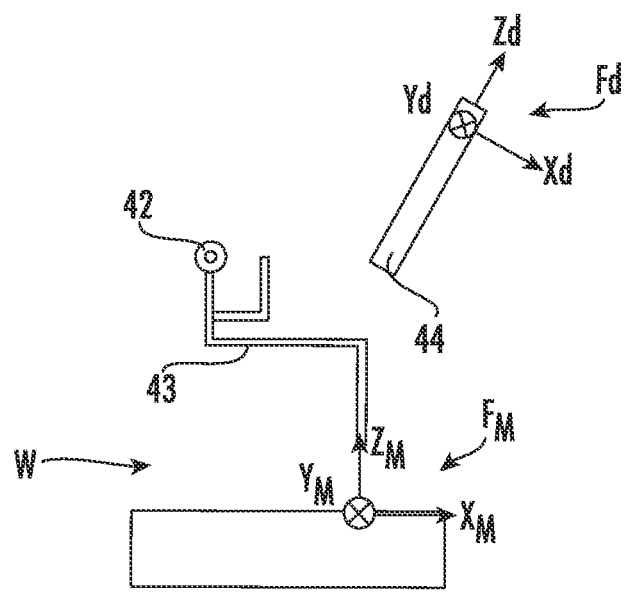
FIG. 2 is a schematic illustration of an exemplary user console of the robotic surgical system of FIG. 1.
Figure 3:
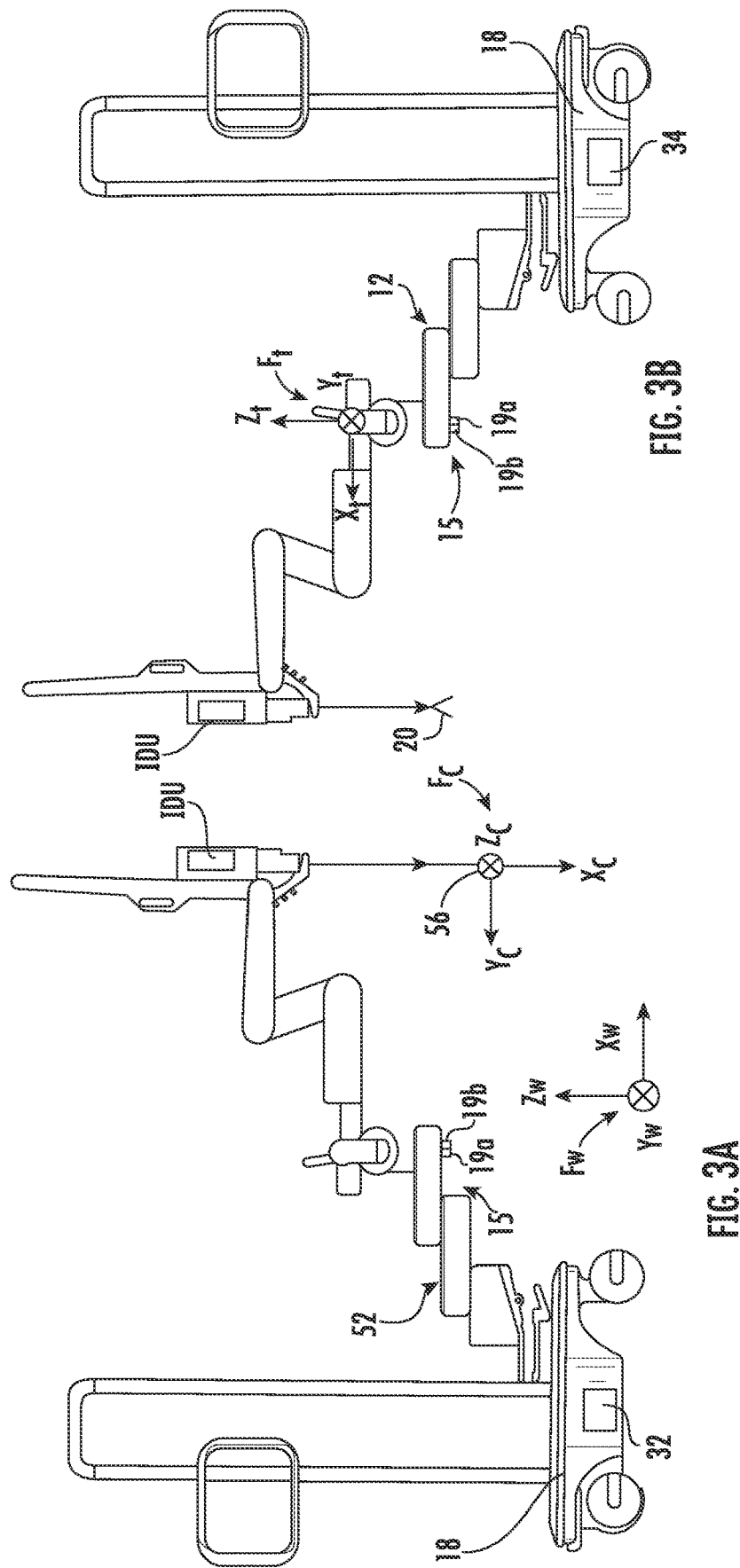
FIGS. 3A and 3B are side views of exemplary robot bases and arms supporting a camera and a tool of the robotic surgical system of FIG. 1.

Referring to FIGS. 1-3B, the robotic surgical system 1 has a world frame $F_w$, the user console 40 has a master frame $F_m$, the display 44 has a display frame Fa, each tool or end effector 20 has a tool frame $F_t$, and the camera 56 has a camera frame $F_c$. The world frame $F_w$ is a fixed frame that is fixed during a surgical procedure defined by the $X_w$-$Y_w$-$Z_w$ axes. With particular reference to FIGS. 3A and 3B, the world frame $F_w$ is a frame positioned on the floor or ground of an operating theater that can be reference by each of the tool frames $F_t$ and the camera frame $F_c$. As shown, the world frame $F_w$ is between the camera arm 52 and the base 18 supporting the tool 20 with the $X_w$ axis being defined in a horizontal direction parallel to the floor, the $Y_w$ axis being defined in a horizontal direction parallel to the floor, and the $Z_m$ axes being defined in a height direction from the floor to the ceiling.

With particular reference to FIG. 2, the master frame $F_m$ is a frame of a workspace W of the user console 40 and is defined by the $X_m$-$Y_m$-$Z_m$ axes. The axes of the master frame $F_m$ are related to input handle 42 and the display 44 with the $X_m$ axis being towards and away from the display 44, the $Y_m$ axis being horizontal or transverse to the display 44, e.g., left/right relative to the display 44, and the $Z_m$ axes being vertical relative to the floor.

Referring back to FIG. 3A, the camera frame $F_c$ is a frame of the camera 56 to define a view of the camera 56 relative to the surgical site S and is defined by the $X_c$-$Y_c$-$Z_c$ axes. The camera frame $F_c$ may be defined for a composite image which is formed from images taken from more than one camera relative to the surgical site S. The $Y_c$ axis and the $Z_c$ axis are perpendicular to one another and are each parallel to a plane defined by a lens of the camera 56. The $X_c$ axis is orthogonal to the plane defined by the lens of the camera 56 and is substantially directed to the surgical site S such that an object distance of the camera 56 is defined along the $X_c$ axis.

Referring to FIG. 3B, the tool frame $F_t$ is a frame of a base 18 supporting the tool 20 to define movement of the tool 20 within the surgical site S relative to the base 18 supporting the tool 20 and is defined by the $X_t$-$Y_t$-$Z_t$ axes. The $X_t$ axis and the $Y_t$ axis are perpendicular to one another and are substantially parallel to the floor. The $Z_t$ axis is perpendicular to each of the $X_t$ and $Y_t$ axes and is substantially vertical towards a ceiling, e.g., away from the floor.

With reference to the robotic surgical system of FIG. 1 and the frames of FIGS. 2-3B, during a medical procedure, the processing unit 30 maps movement of an input handle 42 of the user console 40 in the master frame $F_m$ to a tool 20 assigned to the input handle 42 as it follows movement of the input handle 42 in the respective tool frame $F_t$. For example, as the input handle 42 is moved in a desired direction, e.g., up in the master frame $F_m$, the tool 20 is moved in the tool frame $F_t$ in a direction that corresponds to the desired direction in the display frame Fa, e.g., up as shown on the display 44. To ensure that movement of the input handle 42 in the master frame $F_m$ results in desired movement of the tool 20 in the tool frame $F_t$, the processing unit 30 translates the movement from the master frame $F_m$ to the tool frame $F_t$ by using the positions of the camera frame $F_c$ and the tool frame $F_t$ relative to the world frame $F_w$. To simplify processing, the processing unit 30 may be a distributed processing unit with each base 18 including a controller, e.g., controllers 32, 34, that translate instructions or commands from the central processing unit 30 in the world frame $F_w$ to movements in the respective frame.

As detailed herein, a vector v in a respective coordinate frame r will be expressed as $v_r=[v_x\ v_y\ v_z]$. In addition, a rotation matrix that relates a coordinate frame $F_d$ and a coordinate frame $F_b$ is expressed as $_b{}^aR$ such that $_b{}^aRv_b=v_a$. From this, it will be understood that $_b{}^aR_c{}^bR={}^a{}_cR$ and that $_b{}^aR=({}_a{}^bR)^T$.

As detailed below, the processing unit 30 determines movement in the master frame $F_m$ and translates the movement to the display frame $F_d$. The movement may then be translated to the camera frame $F_c$ which is related to the world frame $F_w$. The relation of the camera frame $F_c$ to the world frame $F_w$ allows the processing unit 30 to translate the movement to the world frame $F_w$. Then the relation between the tool frame $F_t$ and the world frame $F_w$ allows the processing unit 30 to translate the movement from the world frame $F_w$ to the tool frame $F_t$.

To map movement of a respective one of the input handles 42 in the master frame $F_m$ to desired movement of the assigned tool 20 in the tool frame $F_t$, the movement of the input handle 42 in the master frame $F_m$ from a time k−1 to a time k can be expressed as $\Delta p_m=[v_x\ v_y\ v_z]$.

As shown, the display 44 is angled to provide a comfortable view to a clinician interfacing with the user console 40 such that the display frame $F_d$ is offset or rotated relative to the master frame $F_m$. Specifically, the display frame $F_d$ is rotated about the $X_d$ axis at a display angle $\theta_d$ of about 30° or η/6. However, in some embodiments, the display 44 may be positioned to provide a comfortable view to a clinician such that the display frame $F_d$ is substantially aligned with the master frame $F_m$ or at a different display angle $\theta_d$.

When the display frame $F_d$ is offset from the master frame $F_m$, it is necessary to translate movement in the master frame $F_m$ to the display frame $F_d$. To translate movements in the master frame $F_m$ to the display frame $F_d$ the rotation matrix is $$m_d^R = \begin{bmatrix} cos(\theta_d) & 0 & sin(\theta_d) \\ 0 & 1 & 0 \\ -sin(\theta_d) & 0 & cos(\theta_d) \end{bmatrix}$$

such that ΔN, in the display frame $F_d$ can be translated using the transpose of the rotation matrix as $\Delta p_d = ({}_d{}^mR)^T \Delta p_m = {}_m{}^dR \Delta p_m$ which provides $$\Delta p_d = \begin{bmatrix} cos(\theta_d) & 0 & -sin(\theta_d) \\ 0 & 1 & 0 \\ sin(\theta_d) & 0 & cos(\theta_d) \end{bmatrix} \begin{pmatrix} v_x \\ v_y \\ v_z \end{pmatrix}.$$

In some embodiments, the display 44 is capable of displaying an image of the surgical site S that is flipped or rotated about the $Z_d$ axis to allow for a more comfortable manipulation of the tool 20 based on the orientation of the displayed image. In embodiments, the display 44 allows for the flipping of the displayed image by 180° with the manipulation of a single control, e.g., pushing a button or flipping a switch. To translate movements from the display frame $F_d$ to the camera frame $F_c$, a flip rotation matrix $R_f$ for the orientation of the displayed image is applied to the movement in the display frame $F_d$ such that movement in the camera frame $F_c$ is expressed as $\Delta p_c = R_f \Delta p_d$. This flipping of the displayed image by 180° may be represented by a flag such that when the image is flipped the flip flag is "true" or "1" and when the image is not flipped the flip flag is "false" or "0". When the flip flag is false, the flip rotation matrix $R_f$ is $$R_f = \begin{bmatrix} 1 & 0 & 0 \\ 0 & 0 & -1 \\ 0 & 1 & 0 \end{bmatrix}$$

such that movement in a positive $Z_d$ or up on the display 44 is translated to movement of the tool 20 in a negative $Y_c$, movement in a positive $Y_d$ or left on the display 44 is translated to movement of the tool 20 in a positive $Z_c$, and movement in a positive $X_d$ or into the display 44 is translated to movement of the tool 20 in a positive $X_c$. Alternatively, when the flip flag is true, the flip rotation matrix $R_f$ is $$R_f = \begin{bmatrix} 1 & 0 & 0 \\ 0 & 0 & 1 \\ 0 & -1 & 0 \end{bmatrix}$$

such that movement in a positive $Z_d$ or up on the display 44 is translated to movement of the tool 20 in a positive $Y_c$, movement in a positive $Y_d$ or left on the display 44 is translated to movement of the tool 20 in a negative $Z_c$, and movement in a positive $X_d$ or into the display 44 is translated to movement of the tool 20 in a positive $X_c$. It is noted that movement of along $X_d$ is not affected by a condition of the flip flag.

For the surgical robot 10 to move the tool 20, movement of the tool in the camera frame $\Delta p_c$ is translated to movement of the tool in the tool frame $\Delta p_t$. To translate movement of the tool in the camera frame $\Delta p_c$ is translated to movement of the tool in the tool frame $\Delta p_t$, movement of the tool in the camera frame $\Delta p_c$ is first translated to movement of the tool in the world frame $\Delta p_w$. Movement of the tool in the world frame $\Delta p_w$ is then translated to movement of the tool in the tool frame $\Delta p_t$.

To translate movement of a tool or camera, e.g., tool 20 or camera 56, in the world frame $F_w$ to or from a frame of another object, e.g., the camera frame $F_c$ or the tool frame $F_t$, a relation between the world frame $F_w$ and the other frame can be used. For example, the relation between the camera frame $F_t$ and the world frame $F_w$ can be used to translate movement from the camera frame $F_c$ to the movement in the world frame $F_w$. The relationship between the camera frame $F_t$ and the world frame $F_w$ can be determined using a setup arm system 15 utilizing lasers 19a, 19b to determine the relation between the camera and world frames $F_t$, $F_w$. Specifically, the setup arm system 15 includes the lasers 19a, 19b on each robot base 18 to determine a yaw angle $\theta_{yaw}$ and a pitch angle $\theta_{pitch}$ between the respective robot base and the ground, which is a plane of the world frame $F_w$. For a detailed description of a suitable setup arm system and a method for determining a relation between a frame of a robot base and another frame reference can be made to U.S. Provisional Patent Application No. 62/833,876, filed Apr. 15, 2019 (now International Patent Application Serial No. PCT/US2019/036657, filed on Jun. 12, 2019), entitled "SYSTEM AND METHOD FOR ALIGNING A SURGICAL ROBOTIC ARM", the entire contents of which are hereby incorporated by reference.

To translate the camera frame $F_c$ to the world frame $F_w$, the yaw and pitch rotations are applied to the world frame $F_w$ to locate the camera frame $F_c$ within the world frame $F_w$. The order of the rotations is determinative with rotation about the $Z_w$ axis by the yaw angle $\theta_{yaw}$ preceding rotation about the preceding rotation about an intermediate Yi axis (not explicitly shown), which is the $Y_w$ axis rotated by the yaw angle $\theta_{yaw}$ about the $Z_w$ axis, by the pitch angle $\theta_{pitch}$. This provides the following rotation matrix for translating the camera frame $F_c$ to the world frame $F_w$:

$${}_c^wR = \begin{bmatrix} cos(\theta_{yaw}) & -sin(\theta_{yaw}) & 0 \\ sin(\theta_{yaw}) & cos(\theta_{yaw}) & 0 \\ 0 & 0 & 1 \end{bmatrix} \begin{bmatrix} cos(\theta_{pitch}) & 0 & sin(\theta_{pitch}) \\ 0 & 1 & 0 \\ -sin(\theta_{pitch}) & 0 & cos(\theta_{pitch}) \end{bmatrix}$$

In embodiments, the camera 56 is a 0° endoscope such that the rotation matrix for translating the camera frame remains as shown above. However, in some embodiments, the camera 56 may be an offset endoscope such that an additional adjustment rotation matrix $R_a$ of the offset endoscope is required to translate the world frame $F_w$ to the camera frame $F_c$. The adjustment rotation matrix $$R_a = \begin{bmatrix} cos(\theta_a) & -sin(\theta_a) & 0 \\ sin(\theta_a) & cos(\theta_a) & 0 \\ 0 & 0 & 1 \end{bmatrix}$$

where $\theta_a$ is an adjustment angle for the offset of the camera 56. For example, when a 30° offset endoscope is used for the camera 56, the adjustment angle $\theta_a$ is $\pi/6$ such that the adjustment rotation matrix $$R_a = \begin{bmatrix} cos(\pi/6) & -sin(\pi/6) & 0 \\ sin(\pi/6) & cos(\pi/6) & 0 \\ 0 & 0 & 1 \end{bmatrix}.$$

This provides that the rotation matrix for translating the camera frame $F_c$ to the world frame $F_w$, including the adjustment rotation matrix $R_a$, can be expressed as:

$$_c^wR = \begin{bmatrix} cos(\theta_{yaw}) & -sin(\theta_{yaw}) & 0 \\ sin(\theta_{yaw}) & cos(\theta_{yaw}) & 0 \\ 0 & 0 & 1 \end{bmatrix} \begin{bmatrix} cos(\theta_{pitch}) & 0 & sin(\theta_{pitch}) \\ 0 & 1 & 0 \\ -sin(\theta_{pitch}) & 0 & cos(\theta_{pitch}) \end{bmatrix} R_a$$

or, when a 30° offset endoscope is used for the camera 56, expressed as:

$$_c^wR = \begin{bmatrix} cos(\theta_{yaw}) & -sin(\theta_{yaw}) & 0 \\ sin(\theta_{yaw}) & cos(\theta_{yaw}) & 0 \\ 0 & 0 & 1 \end{bmatrix} \begin{bmatrix} cos(\theta_{pitch}) & 0 & sin(\theta_{pitch}) \\ 0 & 1 & 0 \\ -sin(\theta_{pitch}) & 0 & cos(\theta_{pitch}) \end{bmatrix} \begin{bmatrix} cos(\pi/6) & -sin(\pi/6) & 0 \\ sin(\pi/6) & cos(\pi/6) & 0 \\ 0 & 0 & 1 \end{bmatrix}$$

Applying the relation between the camera frame $F_c$ to the world frame $F_w$ to movement in the camera frame $\Delta p_c$ provides movement in the world frame as:

$$\Delta p_w = {}_c^w R R_a \Delta p_c.$$

Now that movement in the world frame $\Delta p_w$ is determined, a relation between the world frame $F_w$ and the tool frame $F_t$ is used to translate movement in the world frame $\Delta p_w$ to movement in the tool frame $\Delta p_t$ such that a rotation matrix ${}_t^w R$ can be determined. As it is necessary to determine the rotation in tool frame $F_t$ from the world frame $F_w$, a transpose of the ${}_t^w R$ rotation matrix is used such that:

$$ {}_w^t R = ({}_t^w R)^T = \left( \begin{bmatrix} cos(\theta_{yaw}) & -sin(\theta_{yaw}) & 0 \\ sin(\theta_{yaw}) & cos(\theta_{yaw}) & 0 \\ 0 & 0 & 1 \end{bmatrix} \begin{bmatrix} cos(\theta_{pitch}) & 0 & sin(\theta_{pitch}) \\ 0 & 1 & 0 \\ -sin(\theta_{pitch}) & 0 & cos(\theta_{pitch}) \end{bmatrix} \right)^T $$

where the $\theta_{yaw}$ and the $\theta_{pitch}$ are taken from the tool frame $F_t$ relative to the world frame $F_w$.

This provides that translating movement in the world frame $\Delta p_w$ to movement in the tool frame $\Delta p_t$ can be expressed as $\Delta p_t = ({}_t^w R)^T \Delta p_w$. Combining this translation with the above translations allows a total transform from the master frame $F_m$ to the tool frame $F_t$ to be expressed as a handeye transformation $T_{handeye}$ such that:

$$T_{handeye} = ({}_t^w R)^T \cdot R_a \cdot {}_c^w R \cdot R_f \cdot {}_m^d R$$

As detailed above, the flip rotation matrix $R_f$ is dependent on a flip flag of the being either true or false to translate the display frame $F_d$ to the camera frame $F_c$. Thus, to translate movement of an input handle 42 to movement of an assigned tool 20 the transformation provides:

$$\Delta p_t = T_{handeye} \Delta p_m$$

The above transformation relies on the camera 56 being stationary during movement of the input handle 42. Thus, when applying the transformation, a camera flag may be included to pause movement of the tool 20 when the camera 56 is moving, rotating, and/or zooming.

Figure 4:
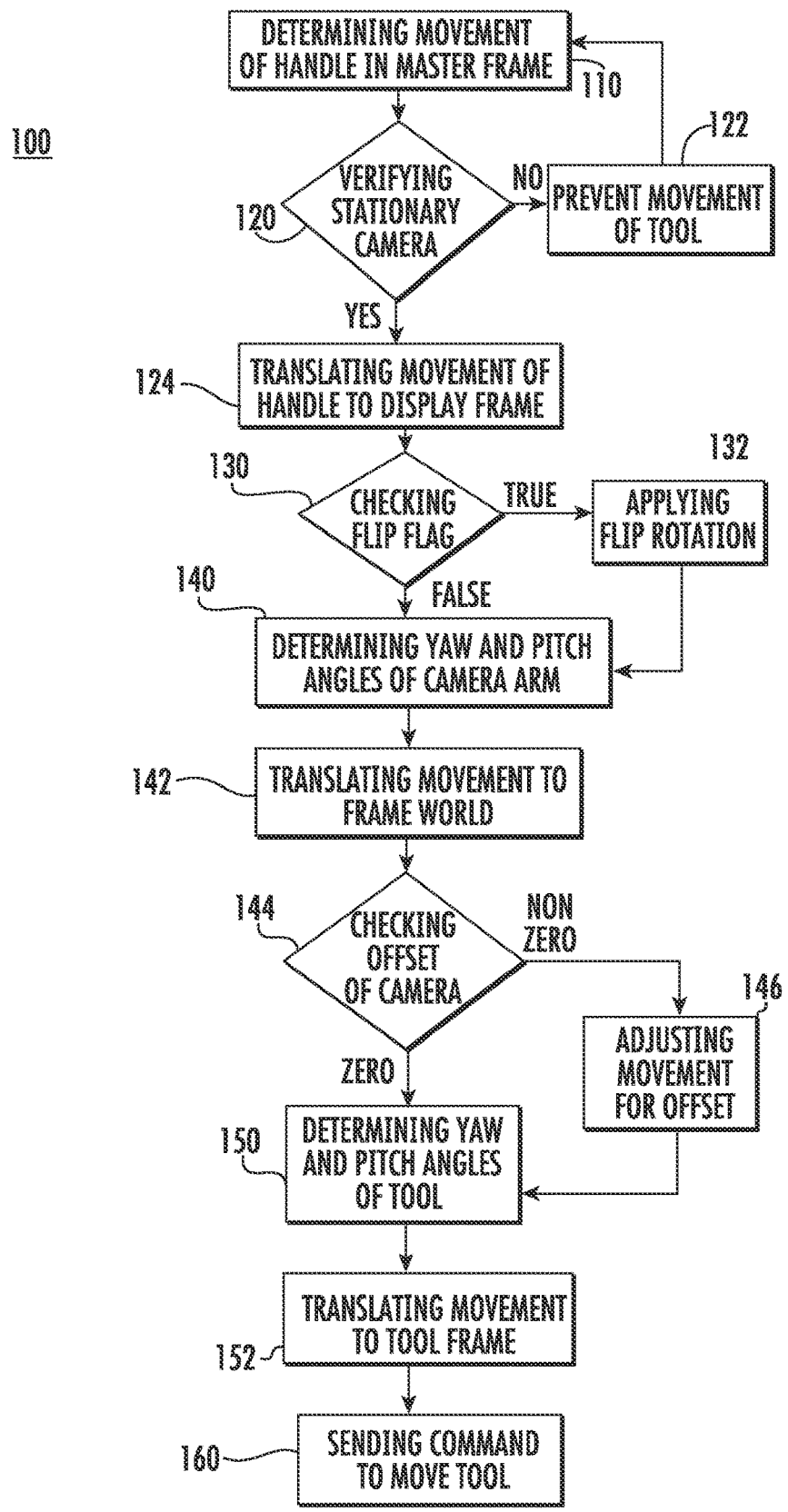
FIG. 4 is a flowchart of a method of translating movement of an input handle of the user console of FIG. 2 to movement of the tool of FIG. 3B.

With reference to FIG. 4, a method 100 of using the transform above to translate movement of an input handle to movement of a tool using a robotic surgical system is described in accordance with the present disclosure with reference to the robotic surgical system 1 of FIGS. 1-3B. The robotic surgical system 1 may be housed in a single location with the user console 40 in the same physical location as the surgical robot 10 or the robotic surgical system 1 may be a teleoperative system with the user console 40 in a remote location, e.g., in another building, city, or country, from the surgical robot 10.

Initially, movement of an input handle 42 of the user console 40 is determined in a master frame $F_m$ by the processing unit 30 (Step 110). The control arm 43 may include encoders and/or motors to determine movement of the input handle 42. For a detailed description of suitable encoders and motors, reference may be made to International Patent Applications No. PCT/US2017/034433, filed May 25, 2017, and PCT/US2017/035580, filed Jun. 2, 2017. The entire contents of each of these applications are hereby incorporated by reference.

Before translating movement of the assigned tool 20, the processing unit 30 verifies that the camera 56, e.g., the camera frame $F_c$, was stationary or fixed during the movement of the input handle 42 (Step 120). The processing unit 30 may include an input in the form of a camera flag that is "True" or "1" when the camera 56 is fixed and is "False" or "0" when the camera is not stationary. When the camera flag is not stationary, the processing unit 30 does not translate movement of the input handle 42 and returns to a ready state for detecting movement of the input handle 42 (Step 122).

When the camera 56 is stationary, the processing unit 30 translates the movement of the input handle 42 from the master frame $F_m$ to the display frame $F_d$ of the display 44 using the rotation matrix ${}_m^d R$ (Step 124). As detailed above, the rotation matrix ${}_m^d R$ accounts for an offset of the display frame $F_d$ from the master frame $F_m$. After the movement is translated to the display frame $F_d$, the processing unit 30 translates the movement to the camera frame $F_c$ (Step 130). To translate the movement to the camera frame $F_c$, the processing unit 30 checks a flip flag to determine if the view provided on the display 44 is flipped from the camera 56 or is not flipped with respect to the camera 56. When the view on the display 44 is flipped, the processing unit applies the flip rotation $R_f$ to the movement (Step 132) before proceeding to translate the movement to the world frame $F_w$. When the image is not flipped from the camera 56, the processing unit 30 may proceed to translate the movement to the world frame $F_w$, without applying the flip rotation $R_f$ or may treat the flip rotation $R_f$ as being equal to 1.

To translate the movement to the world frame $F_w$, the processing unit 30 receives the yaw and pitch angles of an arm 12 supporting the camera 56 (Step 140). The yaw and pitch angles of the arm 12 may be determined by the setup lasers 19a, 19b of the arm 12 and provided by a base 18 supporting the arm 12 to the processing unit 30. A controller 32 within the base 18 may determine and calculate the yaw and pitch angles of the arm 12. The yaw and pitch angles of the arm 12 may are determined for the setup arm 19 and then transferred to the camera 56 by determining positions of joints of the arm 12 supporting the camera 56. With the yaw and pitch angles of the camera 56, the processing unit 30 translates the movement to the world frame $F_w$ using the rotation matrix ${}_c^w R$ (Step 142). Once the processing unit 30 translates movement to the world frame $F_w$, the processing unit 30 checks an offset of the camera 56 (Step 144). When the camera 56 is a zero offset camera, the processing unit 30 proceeds to translate the movement to the tool frame $F_t$ or assigns the adjustment rotation $R_a$ a value of "1". When the offset of the camera 56 is non-zero, the processing unit 30 applies an adjustment rotation $R_a$ to the movement before proceeding to translating movement to the tool frame $F_t$ (Step 146).

With the movement in the world frame $F_w$, the processing unit 30 receives yaw and pitch angles of the tool frame $F_t$ from a base 18 supporting the tool 20. The yaw and pitch angles of the tool frame $F_t$ are determined by the setup lasers 19a, 19b of the arm 12 and provided by the base 18 supporting the arm 12 to the processing unit 30 (Step 150). With the yaw and pitch angles of the base 18 supporting the tool 20, the processing unit 30 translates the movement to the tool frame $F_t$ using the transpose of the rotation matrix ${}_t^w R$ (Step 152).

With the movement translated to the tool frame $F_t$, the processing unit 30 sends control commands to the base 18 supporting the tool 20 such that motors, within the base 18 and/or an instrument drive unit, actuate the arm 12 and/or tool 20 such that the tool 20 is moved in a desired manner in response to movement of the input handle 42 in the master frame $F_m$ (Step 160) such that the tool 20 follows movement of the input handle 42. A controller 34 disposed within the base 18 may receive the control commands and actuate the arm 12 and/or the tool 20 in response to the control commands.

Figure 5:
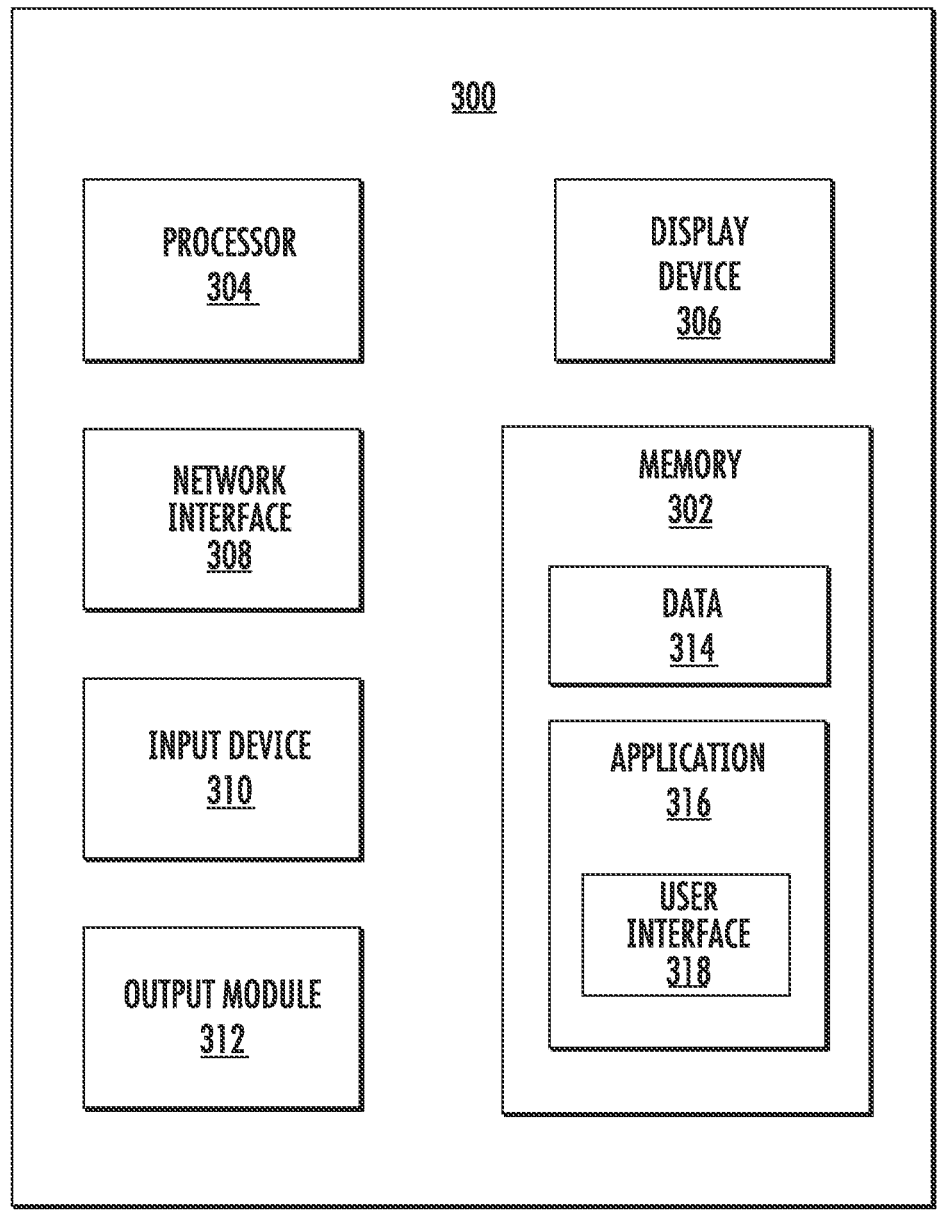
FIG. 5 is a schematic block diagram of an illustrative embodiment of a computing device that may be employed in various embodiment of the present system, for instance, as part of the robotic surgical system of FIG. 1.

Referring to FIG. 5, a computing device may be employed in accordance with various embodiments herein. Although not explicitly shown, in some embodiments, the computing device 300, or one or more of the components thereof, may further represent one or more components (e.g., the processing unit 30, the base 18, the controllers 32, 34, and/or the like) of the robotic surgical system 1. The computing device 300 may, in various embodiments, include one or more memories 302, processors 304, display devices 306, network interfaces 308, input devices 310, and/or output modules 312. The memory 302 includes non-transitory computer-readable storage media for storing data and/or software that is executable by the processor 304 and which controls the operation of the computing device 300. In embodiments, the memory 302 may include one or more solid-state storage devices such as flash memory chips. Alternatively, or in addition to the one or more solid-state storage devices, the memory 302 may include one or more mass storage devices connected to the processor 304 through a mass storage controller (not shown in FIG. 5) and a communications bus (not shown in FIG. 5). Although the description of computer readable media contained herein refers to a solid-state storage, it should be appreciated by those skilled in the art that computer-readable storage media can be any available media that can be accessed by the processor 304. That is, computer readable storage media includes non-transitory, volatile and non-volatile, removable and non-removable media implemented in any method or technology for storage of information such as computer-readable instructions, data structures, program modules or other data. Examples of computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 300.

In some embodiments, the memory 302 stores data 314 and/or an application 316. In some aspects the application 316 includes a user interface component 318 that, when executed by the processor 304, causes the display device 306 to present a user interface (not shown in FIG. 5). The network interface 308, in some embodiments, is configured to couple the computing device 300 and/or individual components thereof to a network, such as a wired network, a wireless network, a local area network (LAN), a wide area network (WAN), a wireless mobile network, a Bluetooth network, the Internet, and/or another type of network. The input device 310 may be any device by means of which a user may interact with the computing device 300. Examples of the input device 310 include without limitation a mouse, a keyboard, a touch screen, a voice interface, and/or the like. The output module 312 may, in various embodiments, include any connectivity port or bus, such as, for example, a parallel port, a serial port, a universal serial bus (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of controlling a tool of a surgical robot with a processing unit such that the tool follows input of an input handle of a user console, wherein the surgical robot includes a first arm supporting a camera and a second arm supporting a tool, the surgical robot defining a world frame, and a range of motion of the second arm defining a tool frame, the second arm being configured to manipulate the tool within the tool frame, the method comprising:
   receiving movement of the input handle in a master frame of the user console;
   translating the movement of the input handle in the master frame to movement of the tool in a camera frame of the camera providing real-time images of a surgical site, the camera defining a camera frame and configured to capture real-time images of a surgical site, wherein translating the movement of the input handle in the master frame to movement of the tool in the camera frame includes applying a flip rotation matrix to movement of the input handle in the master frame to translate movement of the input handle to the camera frame;
   translating the movement of the tool in the camera frame to movement of the tool in the world frame;
   translating the movement of the tool in the world frame to movement of the tool in the tool frame; and
   transmitting control commands to a motor controlling the tool such that the tool follows movement of the input handle.

2. The method according to claim 1, wherein translating the movement of the input handle in the master frame to movement of the tool in the camera frame includes applying a display rotation matrix to movement of the input handle in the master frame to translate movement of the input handle to a display frame of a display of the user console, the display providing visualization of the real-time images of the surgical site.

3. The method according to claim 2, wherein the display rotation matrix rotates the movement 30 degrees about an axis of the master frame.

4. The method according to claim 2, wherein the flip rotation matrix includes rotating movement 180 degrees about an axis of the display frame.

5. The method according to claim 4, further comprising:
   receiving a flip flag; and
   applying the flip rotation matrix when the flip flag indicates that the real-time images from the camera are flipped before being viewed on a display.

6. The method according to claim 1, wherein translating the movement of the tool in the camera frame to the movement of the tool in the world frame includes:
   determining yaw and pitch angles of the camera frame relative to the world frame; and
   applying a world frame rotation matrix including the yaw and pitch angles of the camera frame relative to the world frame to translate the movement of the tool in the camera frame to movement of the tool in the world frame.

7. The method according to claim 1, wherein translating the movement of the tool in the camera frame to the movement of the tool in the world frame includes:
   receiving an offset of the camera; and
   adjusting the movement in the camera frame by the offset of the camera by applying an adjustment rotation matrix including the offset of the camera to the movement of the tool in the camera frame.

8. The method according to claim 1, wherein translating the movement of the tool in the world frame to movement of the tool in the tool frame includes:
   determining yaw and pitch angles of the tool frame relative to the world frame; and
   applying a transpose of a tool frame rotation matrix including the yaw and pitch angles of the tool frame relative to the world frame to translate the movement of the tool in the world frame to movement of the tool frame.

9. The method according to claim 1, further comprising verifying the camera is fixed during the movement of the input handle before transmitting the control commands to the motor controlling the tool.

10. A robotic surgical system comprising:
   a surgical robot including a first arm supporting a camera and a second arm supporting a tool, the camera defining a camera frame and configured to capture real-time images of a surgical site, the second arm defining a tool frame and configured to manipulate the tool within the tool frame, the surgical robot defining a world frame;
   a user console including an input handle and a display, the input handle moveable within a master frame defined by the user console, the display configured to display real-time images of a surgical site provided by the camera; and
   a processing unit configured to:
      receive movement of the input handle in the master frame;
      translate the movement of the input handle in the master frame to movement of the tool in the camera frame, wherein translating the movement of the input handle in the master frame to movement of the tool in the camera frame includes applying a flip rotation matrix to movement of the input handle in the master frame to translate movement of the input handle to the camera frame;
      translate the movement of the tool in the camera frame to movement of the tool in the world frame;
      translate the movement of the tool in the world frame to movement of the tool in the tool frame; and
      transmit control commands to the second arm such that the tool follows movement of the input handle.

11. The robotic surgical system according to claim 10, wherein the display defines a display frame that is rotated relative to one axis of the master frame.

12. The robotic surgical system according to claim 11, wherein the display is rotated 30 degrees about the one axis of the master frame.

13. The robotic surgical system according to claim 10, wherein the display is configured to flip the real-time images provided by the camera 180 degrees before displaying the real-time images.

14. The robotic surgical system according to claim 13, wherein the processing unit is configured to receive a flip flag indicative of the real-time images being flipped on the display and to apply a flip rotation matrix to movement of the tool to translate the movement of the tool to the camera frame.

15. The robotic surgical system according to claim 10, wherein the processing unit is configured to receive yaw and pitch angles of the camera frame relative to the world frame and to apply a world frame rotation matrix including the yaw and pitch angles of the camera frame relative to the world frame to translate the movement of the tool in the camera frame to movement of the tool in the world frame.

16. The robotic surgical system according to claim 10, wherein the processing unit is configured to receive an offset angle of the camera and to apply an adjustment rotation matrix including the offset angle of the camera to adjust the movement of the tool in the camera frame.

17. The robotic surgical system according to claim 10, wherein the processing unit is configured to receive yaw and pitch angles of the tool frame relative to the world frame and to apply a transpose of a tool frame rotation matrix including the yaw and pitch angles of the tool frame relative to the world frame to translate the movement of the tool in the world frame to movement of the tool in the tool frame.

18. The robotic surgical system according to claim 10, wherein the processing unit is configured to verify the camera is fixed during the movement of the input handle before transmitting the control commands.

19. A non-transitory computer-readable medium having stored thereon sequences of instructions that, when executed by a processor, cause the processor to:
   receive movement of an input handle in a master frame of a user console;
   translate the movement of the input handle in the master frame into movement of a tool in a camera frame of a camera providing real-time images of a surgical site, wherein translating the movement of the input handle in the master frame to movement of the tool in the camera frame includes applying a flip rotation matrix to movement of the input handle in the master frame to translate movement of the input handle to the camera frame;
   translate the movement of the tool in the camera frame to movement of the tool in a world frame defined in a surgical theater;
   translate the movement of the tool in the world frame to movement of the tool in a tool frame which is defined by an arm supporting the tool; and
   transmit control commands to a motor controlling the tool such that the tool follows movement of the input handle.

* * * * *